US009861757B2

(12) United States Patent
Moller et al.

(10) Patent No.: US 9,861,757 B2
(45) Date of Patent: Jan. 9, 2018

(54) INJECTION DEVICE WITH AN END OF DOSE FEEDBACK MECHANISM

(71) Applicant: Novo Nordisk A/S, Bagsvaerd (DK)

(72) Inventors: Claus Schmidt Moller, Fredensborg (DK); Bo Radmer, Hilleroed (DK); Lars Ulrik Nielsen, Virum (DK); Christian Peter Enggaard, Vejby (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/241,566

(22) Filed: Aug. 19, 2016

(65) Prior Publication Data
US 2016/0354548 A1 Dec. 8, 2016

Related U.S. Application Data

(63) Continuation of application No. 11/813,389, filed as application No. PCT/EP2006/000486 on Jan. 20, 2006, now Pat. No. 9,457,154.
(Continued)

(30) Foreign Application Priority Data

Jan. 25, 2005 (EP) .................................... 05075187

(51) Int. Cl.
*A61M 5/315* (2006.01)
*A61M 5/20* (2006.01)
*A61M 5/24* (2006.01)

(52) U.S. Cl.
CPC ............ *A61M 5/3157* (2013.01); *A61M 5/20* (2013.01); *A61M 5/24* (2013.01); *A61M 5/3155* (2013.01);
(Continued)

(58) Field of Classification Search
CPC ........ A61M 5/3157; A61M 5/20; A61M 5/24; A61M 5/3155; A61M 2205/581;
(Continued)

(56) References Cited

U.S. PATENT DOCUMENTS 4,592,745 A 6/1986 Rex et al.
5,114,406 A * 5/1992 Gabriel ............... A61M 5/2033
604/134
(Continued)

FOREIGN PATENT DOCUMENTS

DE 19819409 A1 11/1999
EP 594357 A1 4/1994
(Continued)

*Primary Examiner* — Emily Schmidt
*Assistant Examiner* — Lauren M Peng
(74) *Attorney, Agent, or Firm* — Wesley Nicolas

(57) ABSTRACT

An injection device with a dose delivering mechanism being adapted to provide a non-visual, e.g. audible and/or tactile, feedback signal when a set dose has been at least substantially injected. A first and a second part of the injection device are adapted to perform a relative rotational movement with respect to each other. The relative rotational movement causes at least two parts of the injection device to abut or engage, and this abutment or engagement causes the non-visual feedback signal to be generated. A very distinct and precise feedback is provided as compared to prior art axial solutions because the generation of the feedback signal is initiated by the relative rotational movement.
Feedback signal may be generated by a change in a rotational velocity of at least one part, e.g. by changing the pitch of a threaded portion or by engaging a non-rotating part and a rotating part, thereby causing the non-rotating part to start rotating. May alternatively be generated by building up and releasing a tension.
The injection device is suitable for injecting insulin.

12 Claims, 14 Drawing Sheets

Related U.S. Application Data

(60) Provisional application No. 60/647,491, filed on Jan. 27, 2005.

(52) U.S. Cl.
CPC ..... *A61M 5/31535* (2013.01); *A61M 5/31551* (2013.01); *A61M 5/31561* (2013.01); *A61M 5/31585* (2013.01); *A61M 2205/581* (2013.01); *A61M 2205/582* (2013.01)

(58) Field of Classification Search
CPC ........ A61M 2205/582; A61M 5/31535; A61M 5/31551; A61M 5/31585
See application file for complete search history.

(56) References Cited

U.S. PATENT DOCUMENTS

| | | | | |
|---|---|---|---|---|
| 5,391,157 | A | * | 2/1995 | Harris ............... A61M 5/31511 604/208 |
| 5,501,670 | A | * | 3/1996 | Sak ................... A61M 5/31511 604/110 |
| 5,582,598 | A | * | 12/1996 | Chanoch ........... A61M 5/31551 222/309 |
| 5,957,889 | A | | 9/1999 | Poulsen et al. |
| 6,004,297 | A | | 12/1999 | Steenfeldt-Jensen et al. |
| 6,221,046 | B1 | | 4/2001 | Burroughs et al. |
| 6,248,090 | B1 | | 6/2001 | Jensen et al. |
| 6,277,098 | B1 | | 8/2001 | Klitmose et al. |
| 6,454,743 | B1 | | 9/2002 | Weber |
| 6,663,602 | B2 | | 12/2003 | Moller |
| 6,699,224 | B2 | | 3/2004 | Kirchhofer et al. |
| 6,796,970 | B1 | | 9/2004 | Klitmose et al. |
| 7,241,278 | B2 | | 7/2007 | Moller |
| 8,202,256 | B2 | | 6/2012 | Moller |
| 8,206,361 | B2 | | 6/2012 | Moller |
| 8,267,899 | B2 | | 9/2012 | Moller |
| 8,333,739 | B2 | | 12/2012 | Moller |
| 2004/0210199 | A1 | | 10/2004 | Atterbury et al. |

FOREIGN PATENT DOCUMENTS

| | | |
|---|---|---|
| EP | 688571 A1 | 12/1995 |
| JP | 2002-503116 A | 1/2002 |
| JP | 2002-513647 A | 5/2002 |
| RU | 2212254 | 9/2003 |
| SU | 1528330 A3 | 12/1989 |
| WO | 9857688 | 12/1998 |
| WO | 99/56805 A1 | 11/1999 |
| WO | 2004007002 A1 | 1/2004 |

\* cited by examiner

INJECTION DEVICE WITH AN END OF DOSE FEEDBACK MECHANISM

CROSS-REFERENCE TO RELATED APPLICATIONS

This application is a continuation of application Ser. No. 11/813,389, filed Jul. 5, 2007 (Notice of Allowance received), which is a 35 U.S.C. §371 national stage application of International Patent Application PCT/EP2006/000486 (published as WO 2006/079481), filed Jan. 20, 2006, which claimed priority of European Patent Application 05075187.4, filed Jan. 25, 2005; this application further claims priority under 35 U.S.C. §119 of U.S. Provisional Application 60/647,491, filed Jan. 27, 2005; the contents of which are incorporated herein by reference.

FIELD OF THE INVENTION

The present invention relates to an apparatus for delivering liquid drugs to a mammal, preferably a human being, preferably in a subcutaneous manner. More particularly, the present invention relates to an injection device which is capable of providing a non-visual feedback signal to a user indicating that a set dose has been injected by the injection device.

BACKGROUND OF THE INVENTION

In the present disclosure reference is mainly made to the treatment of diabetes by injection of insulin. However, this is merely an exemplary use of the present invention. Thus, the present invention may be used for injection of any other suitable kind of drug, e.g. growth hormone.

Injection devices, e.g. in the form of injection pens, are mainly made for users who have to inject themselves frequently, e.g. people having insulin-dependent diabetes or needing treatment by growth hormones. A number of requirements are set to such injection devices. The setting of a dose must be easy and unambiguous and it must be easy to read the set dose. Furthermore, it must be possible, with a minimum of trouble, to cancel or change a wrongly set dose. Finally, when the dose is injected the dose setting mechanism must return to zero. This is very important since it ensures that the set dose is actually injected, thereby allowing the user to keep track of which dose is injected.

Many injection devices work with a threaded piston rod which cooperates with a nut, the nut and the piston being capable of rotating relatively to each other. The dose setting may be obtained by dialling the nut away from a stop to which it is returned during injection by pressing the piston rod forward, either manually or by means of a mechanically biased mechanism, such as a spring, until the nut member abuts the stop. In other injection devices one of the elements, the nut or the piston rod, is kept inrotatable while the other one is allowed to rotate a set angle depending on the set dose, whereby the piston rod is dialled a distance in a forward direction through the nut member.

In such prior art injection devices a dose is normally set by dialling a dose setting member, and the set dose is injected by pushing an injection button. In elongated pen shaped injection devices the dose setting member and the injection button normally form a single member. When the injection button is pushed the set dose is expelled. However, the amount of drug expelled is only equal to the set dose if the injection button has been pushed as far as possible, the dose setting member thereby having been brought back to zero. In order to ensure that the correct dose has actually been injected, the user therefore has to visually inspect the position of the dose setting member during the injection. This is disadvantageous because the injection in some cases will take place in a part of the body where visual inspection during the injection is very difficult or even impossible. Furthermore, in case the user is visually impaired it may be difficult for the user to visually inspect the dose setting member during or after the injection, regardless of where on the body the injection is performed. Since it is not uncommon for people having diabetes to be visually impaired, this is an important aspect.

It is therefore desirable to provide a feedback signal to the user indicating that the set dose has been injected, the feedback signal being of a kind which makes it unnecessary for the user to visually inspect whether or not the set dose is injected.

Some prior art injection devices have a mechanism which informs the user that a dose is being injected by producing an audible 'click' for each dose unit being injected. However, since these clicks appear during the entire injection they do not provide a feedback signal indicating that the set dose has been injected, and the problem indicated above is therefore not solved by these injection devices. Prior art injection devices of this type are, e.g., described in U.S. Pat. No. 4,592,745, EP 0 688 571 and US 2004/0210199.

In WO 98/57688 an injection device is disclosed which addresses the above mentioned problem. Thus, WO 98/57688 discloses an injection device having a dose setting device. A dose is set by dialling a dose setting member. Apart from setting a dose the dialling action causes an injection button to be moved from a position where it abuts a housing of the injection device to a position where it protrudes from the housing. The set dose is subsequently delivered by pushing the injection button back into abutment with the housing.

In one embodiment a lock is activated when the injection button reaches the housing, and the activation of the lock produces an audible click indicating that the injection button is in abutment with the housing and thereby that the set dose has been delivered. During the injection, including the final part when the lock is activated, the injection button is moved linearly. The linear distance travelled by the injection button during the last few doses is relatively short. It may therefore be difficult to determine accurately from the audible click produced by the lock whether or not and when the set dose has been delivered.

EP 0 594 357 discloses another injection device which addresses the above mentioned problem. Thus, EP 0 594 357 discloses an injection device having a top section with resilient legs depending perpendicularly from the top section. The outer surface of the resilient legs has a ridge which rests on a ledge inside of the dose knob. The dose knob may have an elongated section which fits into a cylindrical sleeve such that when the dose knob is pushed into the sleeve, at the end of injection, the top portion of the sleeve touches end of the leg of the resilient legs displacing the ridge from the ledge and causing a snapping noise. As it is the case with the injection device described in WO 98/57688, the dose knob is moved linearly during injection, also during the final part of the injection when the resilient legs are displaced from the ridge causing the snapping noise. Therefore the shortcomings described above are also applicable here.

SUMMARY OF THE INVENTION

It is, thus, an object of the present invention to provide an injection device being capable of precisely and in a non-visual manner indicating to a user when a set dose has been injected.

It is a further object of the present invention to provide an injection device being capable of non-visually indicating to a user when a set dose has been injected, the indication being delivered to the user in a very distinct manner.

It is an even further object of the present invention to provide a dose delivering mechanism for an injection device, the dose delivering mechanism being capable of precisely and in a non-visual manner indicating to a user when a set dose has been injected.

According to the present invention the above and other objects are fulfilled by providing an injection device comprising:
- a housing,
- a dose setting member being operable to set a desired dose to be injected,
- a piston rod being adapted to cooperate with a piston so as to cause a set dose to be injected from an ampoule, and
- a dose delivering mechanism being adapted to operate the piston rod in such a way that a set dose is injected, the dose delivering mechanism further being adapted to provide a non-visual feedback signal to a user only at the end of injection of a set dose, wherein first and second parts of the injection device are adapted to perform a relative rotational movement with respect to each other during injection of a dose, and wherein said relative rotational movement causes at least two parts of the injection device to abut or engage, said abutment or engagement causing the non-visual feedback signal to be generated.

The injection device of the present invention is very suitable for use by persons which have to frequently inject themselves, e.g. persons having insulin-dependent diabetes or needing treatment by growth hormones. The desired dose being set by means of the dose setting member is, thus, a dose of a specific drug which the person in question needs to inject at that specific point in time. The desired dose may be a fixed dose which the person needs to inject each time an injection is performed, or it may be a varying amount, e.g. varying according to the time of day and/or one or more parameters which may be measured or chosen prior to setting the dose (e.g. blood glucose (BG) level, contents of a meal, etc.).

The piston rod is preferably adapted to push a piston into an ampoule, thereby causing the set dose to be injected. This may be obtained in various ways and is well known and well described in the art.

The dose delivering mechanism is adapted to provide a non-visual feedback signal to a user only at the end of injection of a set dose. Thus, the feedback signal may be generated when the set dose has been injected, e.g. exactly when or immediately after the last unit has been injected. Alternatively, the feedback signal may be generated before the complete dose has been delivered, e.g. when a few units remain to be injected, the remaining units being injected while the feedback signal is sensed by the user. Thus, when the user perceives the feedback signal the set dose will have been delivered, and the user will therefore not be able to tell the difference between a feedback signal being generated after the dose has been completely injected and a feedback signal being generated immediately before the dose has been completely injected. In any event the user can regard the perception of the feedback signal as an indication that the set dose has been delivered, and the user may therefore react correspondingly, e.g. by removing a pressure applied manually to an injection button.

Since the non-visual feedback signal is provided only at the end of injection of a set dose the user will know distinctly that when the feedback signal is received the set dose has been fully injected. This is an advantage compared to prior art injection devices where a click for each injected dose unit is produced. In this case the user would have to count the number of clicks produced and compare this to the number of set dose units in order to tell exactly when the set dose has been fully injected.

A first part and a second part of the injection device are adapted to perform a relative rotational movement with respect to each other during injection of a dose. This may, e.g., be the housing and the piston rod, or it may be a separate member and any other part of the injection device, e.g. the housing and/or the piston rod, the sole purpose of the separate member being to generate the non-visual feedback signal. Three or more parts of the injection device may perform mutual rotational movements during injection of a dose.

Furthermore, the relative rotational movement may be performed all through the injection of a dose or it may be performed during only part of the injection. Thus, the relative rotational movement may be started or stopped at the end of injection of a set dose as defined above, in which case this starting or stopping may advantageously cause the non-visual feedback signal to be generated.

The relative rotational movement causes at least two parts of the injection device to abut or engage, and this abutment or engagement causes the non-visual feedback signal to be generated. One or both of the parts which abut or engage may be the first and/or second parts, i.e. the parts performing the relative rotational movement. Alternatively, one or both of the parts which abut or engage may be other parts of the injection device. This will be described in further details below.

Due to the fact that the relative rotational movement initiates the generation of the non-visual feedback signal it is ensured that the movement generating the non-visual feedback signal is much longer than a corresponding movement in an injection device where the feedback signal is generated by a linear movement of one or more parts. Thereby the generated signal will be much more precise and distinct, and a far more accurate feedback signal has thereby been provided. This is very advantageous because it makes it much easier for the person to ascertain that the expected and desired dose has actually been injected.

The non-visual feedback signal may comprise an audible and/or a tactile signal. In this case the person using the injection device will be able to hear and/or feel that the set dose has been injected. Alternatively or additionally, the non-visual feedback signal may comprise any other suitable kind of signal which can be perceived by other senses than sight. Furthermore, the non-visual feedback signal may be followed by a visual signal, e.g. a scale drum showing a 'zero', a lamp or a diode which is turned on or off or starts flashing simultaneously with the generation of the non-visual feedback signal. Thereby the user may, in addition to the non-visual feedback signal, use this visual feedback signal to further ensure that the set dose has actually been injected.

In one embodiment of the present invention the abutment or engagement is caused by a change in a rotational velocity of at least one part of the dose delivering mechanism. This may, e.g., be accomplished by allowing a separate member to start rotating at the end of injection of a set dose, typically in such a way that this member rotates during injection of the last few units of the set dose. The rotation of this separate member will in turn generate a non-visual feedback signal to the user. Thus, in this case the rotational velocity of this member relatively to, e.g., the housing, changes from zero to a certain velocity, and this change causes the non-visual feedback signal to be generated, e.g. in the form of a clicking sound generated by protruding parts present on the separate member moving against an inner part of the housing or an outer part of the piston rod.

Alternatively or additionally, the change in rotational velocity may cause a tactile feedback signal to be generated. It may, e.g., be possible to feel the rotational movement itself, and thereby it may be possible for the user to detect a substantial change (decrease or increase) in the rotational velocity.

In one embodiment the injection device may further comprise a ratchet operating the piston rod and having a threaded portion being adapted to engage with a part of the dose delivering mechanism, in which case the change in a rotational velocity is generated by a change in the pitch of the threaded portion of the ratchet, said change in the pitch in return causing a change in a translational velocity of said part of the dose delivering mechanism, said change in translational velocity causing at least two parts of the injection device to abut, thereby causing the non-visual feedback signal to be generated.

In this embodiment the non-visual feedback signal preferably comprises a tactile feedback signal. Thus, the part of the dose delivering mechanism which is adapted to engage with the threaded portion of the ratchet is preferably in directly or indirectly contact with the user during injection of a dose. Thus, the part may be, form part of or be operatively connected to an injection button which the user presses during injection. Thereby the user will be able to feel the change in translational velocity.

The pitch may be changed from a certain value used during the main part of the injection to zero, i.e. the threaded portion simply stops at a position corresponding to the end of injection of a set dose. In this case the user will feel a kind of 'axial resistance' during the injection until the ratchet/dose delivery part reaches the position where the threaded portion stops. Then the part will stop rotating and instead increase the velocity of a translational (axial) movement which is also performed while the ratchet/dose delivery part travels the threaded portion, due to the pitch of the threaded portion. The user will be able to feel this increase in translational velocity. Furthermore, the translational movement is preferably eventually stopped, e.g. due to part of the dose delivery mechanism abutting a stop member. This stop will also be very distinctly felt by the user, thereby producing a non-visual feedback signal, and it may further produce a sound, in which case the non-visual feedback signal comprises a tactile as well as an audible signal. In this embodiment the two parts of the injection device which are caused to abut may advantageously be a scale drum and a part of the housing, the scale drum performing a rotational and axial movement defined by the threaded portion.

Alternatively, the two parts may be a dose knob and a proximal part of the housing, the dose knob performing an axial movement which follows the axial part of the movement of the scale drum as described above.

Alternatively, the pitch may either increase or decrease from one non-zero value to another. This has the advantage that the engaging part is readily moved back into engagement with the threaded portion when a new dose is to be set.

In another embodiment the dose delivering mechanism may comprise a first dose part and a second dose part, the first dose part being adapted to rotate relatively to the housing during injection of a dose and the first dose part comprising means for engaging the second dose part at the end of injection of a set dose, thereby causing the second dose part to rotate along with the first dose part, in which case the non-visual feedback signal is generated by the resulting rotational movement of the second dose part.

In this embodiment the rotational movement of the second dose part increases from zero to a non-zero value at the end of injection of the set dose. The second dose part may be provided with teeth, protrusions, flexible arms or similar means being adapted to be moved against another part of the device during rotation of the second dose part, thereby producing a sound which at least partly constitutes the non-visual feedback signal.

The second dose part may be positioned between the first dose part and the housing. In case the second dose part is provided with teeth, protrusions, flexible arms or the like as described above, these may advantageously be moved against a part of the housing when the second dose part is rotated along with the first dose part.

Alternatively, the non-visual feedback signal may be generated as a result of an abutment between two parts of the dose delivering mechanism performing a relative rotational movement. The feedback signal may, e.g., be obtained by releasing a tension which has previously been introduced in a part of the injection device, the release of the tension being caused by the abutment between the two parts.

The tensed part may comprise a spring means, such as a separate spring member or at least one resilient portion of at least one of the first and second parts performing the relative rotational movement. In case the spring means is in the form of at least one resilient portion of the part(s) the non-visual feedback signal may be generated in the following manner. First the resilient portion(s) is/are bent into a tensed position. At a later time this tension is released, e.g. by rotating the resilient portion(s) away from a part which holds the resilient portion(s) in the tensed position. Thereby the resilient portion(s) will restore its/their relaxed position(s), and this movement will generate a clicking sound, i.e. a non-visual feedback signal. The resilient portion(s) may be in the form of spring arm(s), in which case a sound may be generated due to moving air caused by sudden release of the tensed spring arm(s). Alternatively, abutment between a moving part and a release mechanism may release the tension of the resilient portion(s).

The tension may be introduced during dose setting, e.g. by tightening a spring member or moving a resilient portion into a tensed position as described above. This may be obtained by letting the dose setting mechanism be connected to a spring member, e.g. in such a way that a spring is tightened when a dose setting member is turned, or in such a way that a part being provided with a resilient portion is rotated along with a dose setting member, thereby causing the resilient part to be moved into a tensed position.

Alternatively, the tension may be introduced during injection of a dose. This may be obtained in a manner very similar to what is described above. However, in this case the tensed part should be operatively connected to the dose delivering mechanism.

The dose delivering mechanism may be adapted to be manually operated, e.g. by means of an injection button which the user must press manually during the injection.

Alternatively, the dose delivering mechanism may be adapted to be operated by means of a mechanically biased mechanism, e.g. comprising at least one spring. The mechanically biased mechanism may, in this case, be biased during setting of a dose. When the injection is subsequently performed this is done by releasing the tension previously built up in the mechanically biased mechanism, and the stored energy will then cause the set dose to be injected. This kind of injection device does not require a force applied by the user in order to inject a set dose.

BRIEF DESCRIPTION OF THE DRAWINGS

The invention will now be further described with reference to the accompanying drawings in which.

The Figures are schematic and simplified for clarity, and they only show details which are essential to the understanding of the invention while other details are left out. Throughout the description of the drawings the same reference numerals will be used for identical or corresponding parts.

DETAILED DESCRIPTION OF THE DRAWINGS

When in the following terms as 'upper' and 'lower', 'left' and 'right', 'horizontal' and 'vertical', 'clockwise' and 'counter clockwise' or similar relative expressions are used, these only refer to the accompanying drawings and not to the actual situation of use. The shown Figures are schematic representations for which reason the configuration of the different structures as well as their relative dimensions are intended to serve illustrative purposes only. In that context it may be convenient to define that the term 'distal end' in the accompanying drawings is meant to refer to the end of the injection device carrying an injection needle, whereas the term 'proximal end' is meant to refer to the opposite end pointing away from the injection needle.

Figure 1:
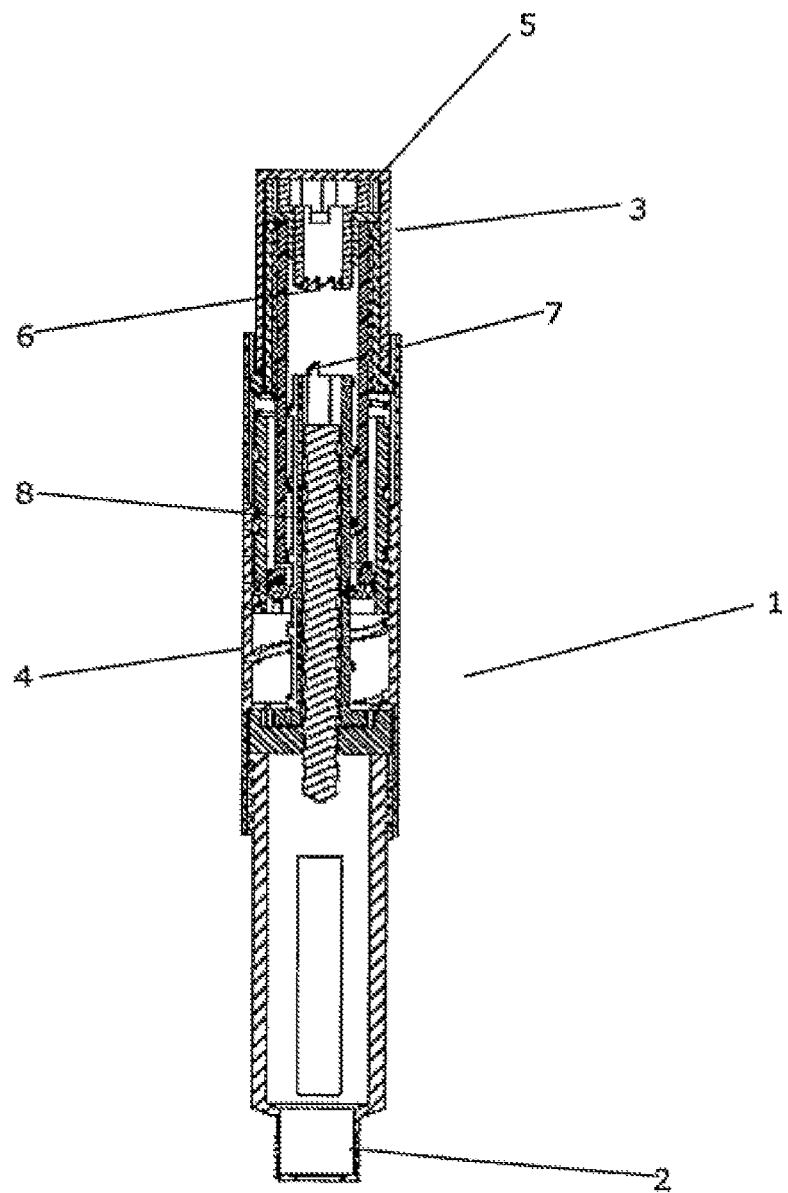
FIG. 1 shows a cross section through an injection device according to a first embodiment of the invention and being in a position where a dose has been set.

FIG. 1 shows a cross section through an injection device 1 according to a first embodiment of the invention. At its distal end the injection device 1 is provided with a portion 2 being adapted to carry an injection needle (not shown). At its proximal end the injection device 1 comprises a combined dose setting and injection button 3. During dose setting the dose setting and injection button 3 is rotated. This causes the dose setting and injection button 3 to be moved away from a housing 4 to the position shown in FIG. 1. During injection the user presses the dose setting and injection button 3, thereby moving it back into the housing 4.

This movement causes the set dose to be injected from the injection device 1. Inside the dose setting and injection button 3 there is positioned a click item 5 which is provided with a set of teeth 6 being adapted to engage with a corresponding tooth 7 positioned on a ratchet 8. During injection the ratchet 8 will rotate relatively to the housing 4 while the click item 5 will not rotate.

Figure 2:
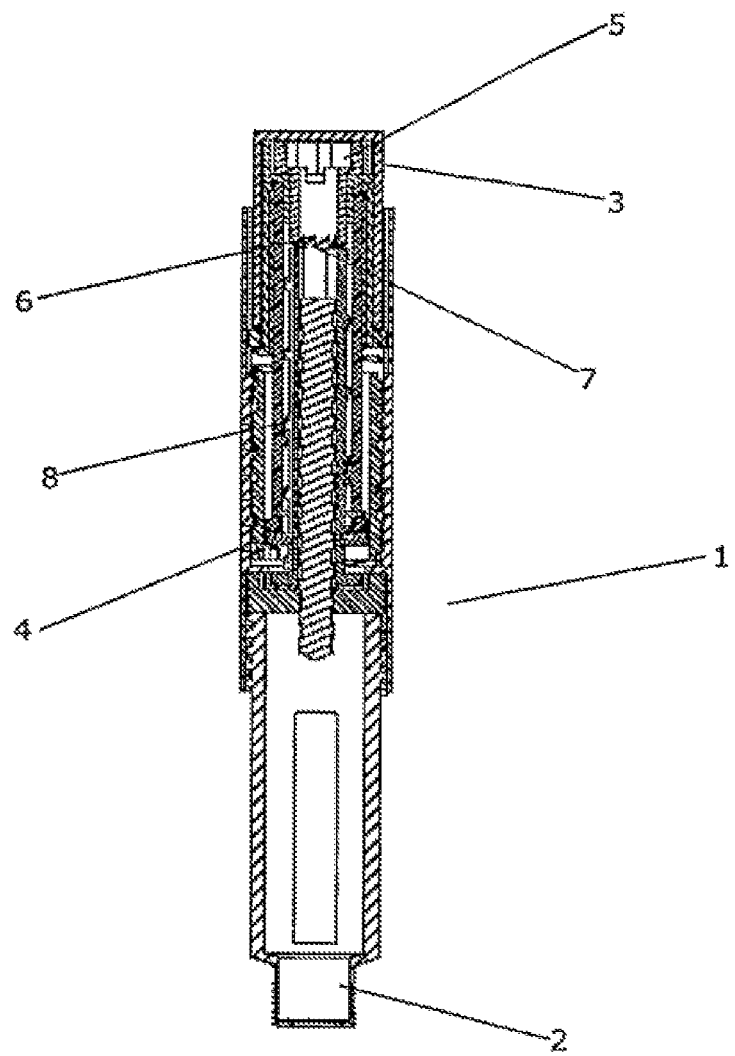
FIG. 2 shows a cross section through the injection device of FIG. 1 in a position where a dose has been injected.

FIG. 2 shows a cross section of the injection device 1 of FIG. 1. However, in FIG. 2 a dose has just been injected, i.e. the dose setting and injection button 3 has been pushed to a position inside the housing 4. Thereby the set of teeth 6 on the click item 5 engage with the tooth 7 on the ratchet 8. Since the ratchet 8 rotates during the injection, this will cause the click item 5 to be rotated along with the ratchet 8. This rotational movement will cause the click item 5 to produce a sound in a manner which will be explained further below with reference to FIG. 3. Since the click item 5 is only rotated during the injection of the last few units of the set dose the produced sound indicates that the set dose has been substantially injected. Thereby a non-visual feedback signal has been generated.

Figure 3:
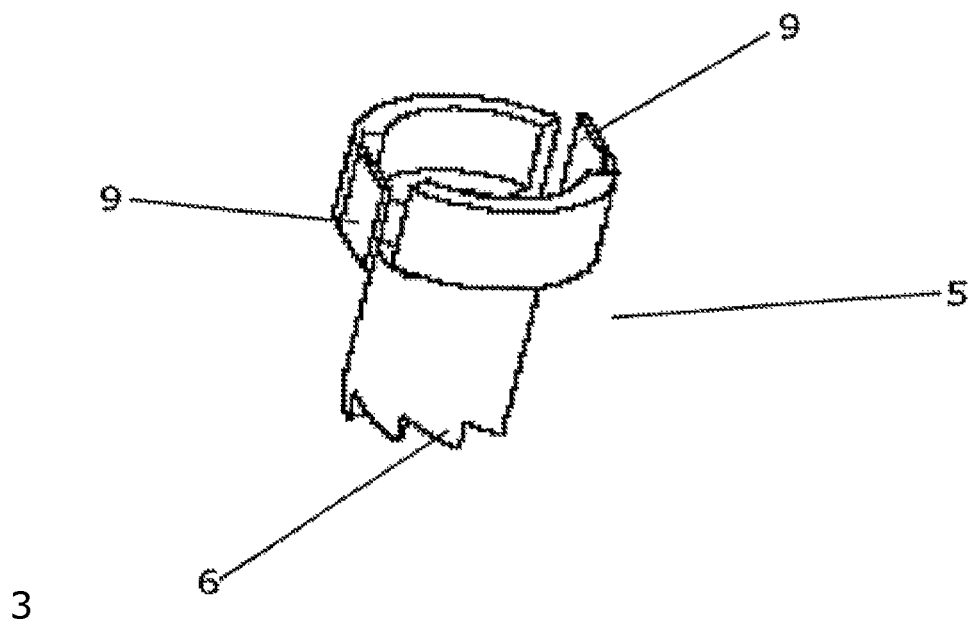
FIG. 3 shows a click item adapted to be positioned in the injection device of FIGS. 1 and 2.

FIG. 3 is a perspective view of a click item 5 adapted to be inserted in the injection device 1 of FIGS. 1 and 2. The part of the click item 5 positioned opposite the set of teeth 6 is provided with two resilient parts 9. The resilient parts 9 are resilient due to a reduced thickness of the material making up the parts 9 as compared to the thickness of the material making up the remaining parts of the click item 5. When the click item 5 is rotated as described above the resilient parts 9 will be moved against the inner part of the housing 4, and this will cause the resilient parts 9 to be alternatingly tensed and released. Each time the resilient parts 9 are released they will produce a clicking sound, thereby generating the non-visual feedback signal.

Figure 4:
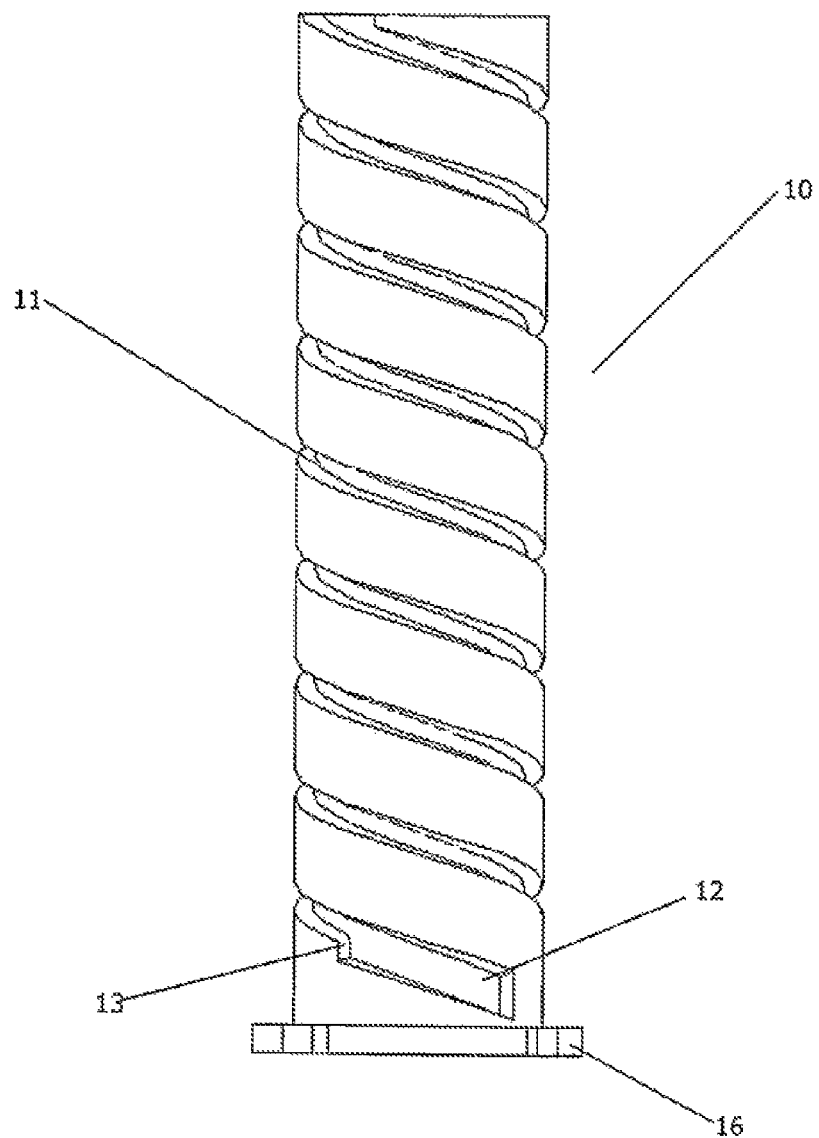
FIG. 4 shows a threaded inner part being adapted to be positioned in an injection device according to a second embodiment of the invention.

FIG. 4 shows a threaded inner part 10 being adapted to be inserted inside a housing of an injection device according to a second embodiment of the invention. The main part of the thread 11 has a constant pitch. However, in the lower part of the thread 12 the pitch is abruptly decreased. This can be seen in the form of an axial edge 13. Thereby a part engaging with the thread 11, 12 will be moved abruptly relatively to the inner part 10 along an axial direction when the engaging part reaches the lower part of the thread 12, i.e. when it reaches the axial edge 13. This abrupt movement, and not the least the following abrupt stop when this movement stops, can be felt by the user as will be described below. Furthermore, the location of the axial edge 13 towards the end of the threaded portion 12 ensures that the felt abrupt movement indicates the end of injection of a set dose. Thereby a non-visual (tactile) feedback signal has been provided as a result of a change in the pitch of a threaded portion 11, 12.

Figure 5:
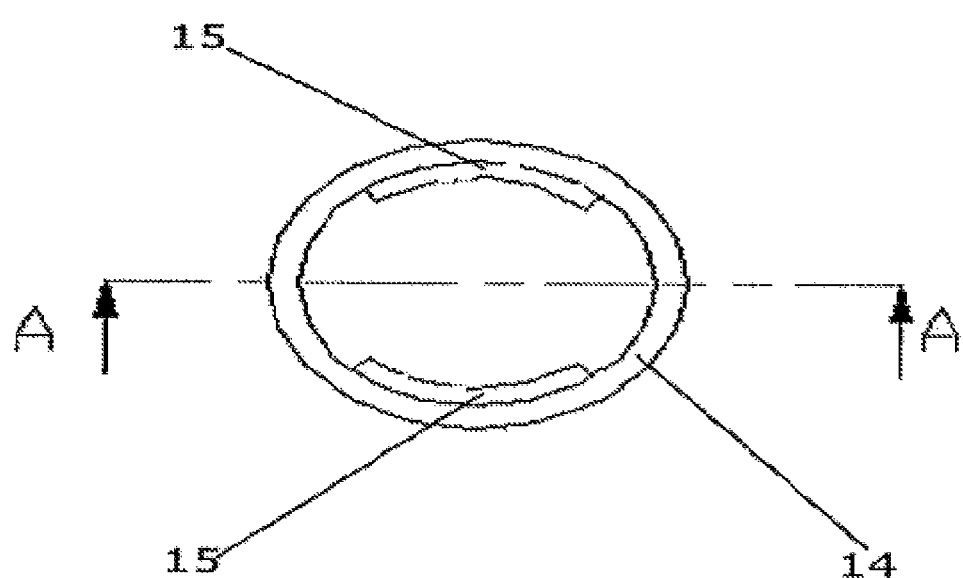
FIG. 5 shows a top view of an outer part being adapted to engage with the inner part of FIG. 4.

FIG. 5 shows a top view of an outer part 14 being adapted to be positioned around the threaded inner part 10 of FIG. 4. The outer part 14 is provided with two protruding parts 15 each being adapted to engage with the thread 11, 12 of the inner part 10.

Figure 6:
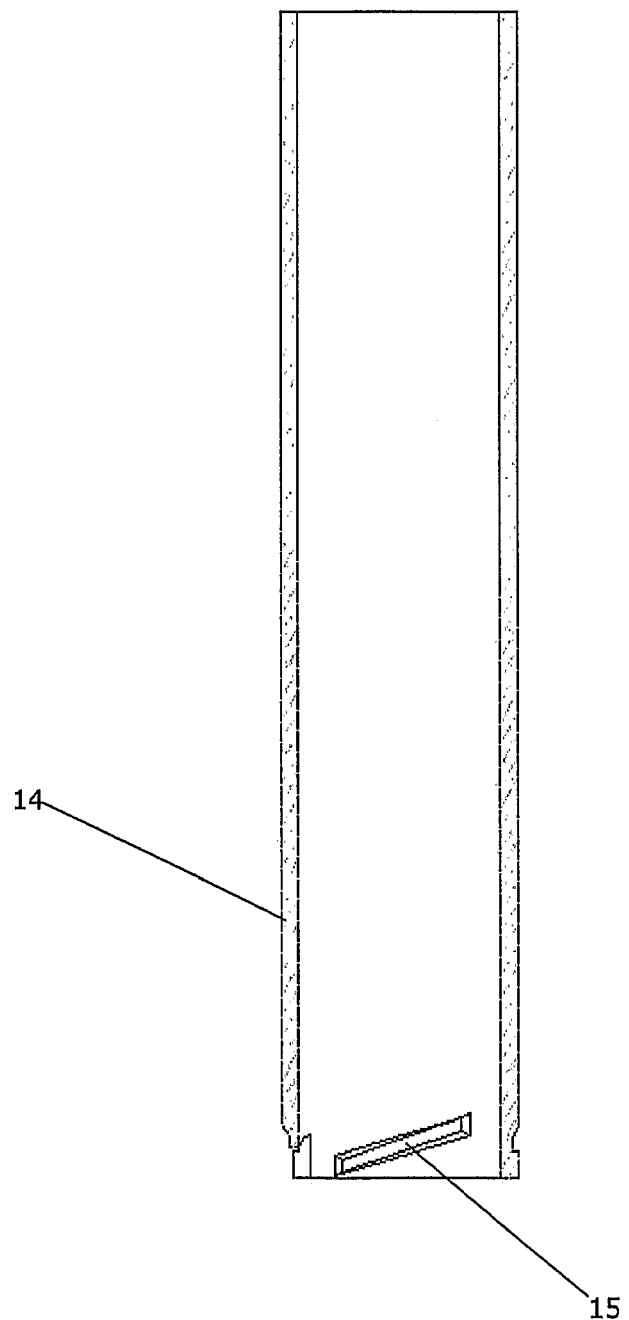
FIG. 6 is a cross section along line A-A in FIG. 5, FIGS. 7-10 show parts of injection devices according to a third, fourth, fifth and sixth embodiment of the invention, respectively, all having a spring arm and a wedge structure.

FIG. 6 shows a cross section through the outer part 14 shown in FIG. 5 along the line A-A. During injection of a dose the inner part 10 and the outer part 14 will initially be relatively positioned in such a way that the protruding parts 15 engage with the part of the thread 11 being positioned opposite the lower part of the thread 12. The outer part 14 is then pushed inwards, thereby allowing the protruding parts 15 to travel the threaded portion 11. Due to the thread 11 the inner part 10 and the outer part 14 perform a relative rotational movement. When the protruding parts 15 reach the axial edge 13 the axial velocity of the outer part 14 will increase abruptly as described above, and because the user is manually pressing the outer part 14 this abrupt movement, as well as the abrupt stop occurring when the outer part 14 abuts a stop member 16 present on the inner threaded part 10 (see FIG. 4), will be felt by the user. Thereby a tactile feedback signal is provided. Furthermore, the outer part 14 abruptly abutting the stop member 16 may produce a sound, thereby providing an audible feedback signal in addition to the tactile feedback signal.

Figure 7:
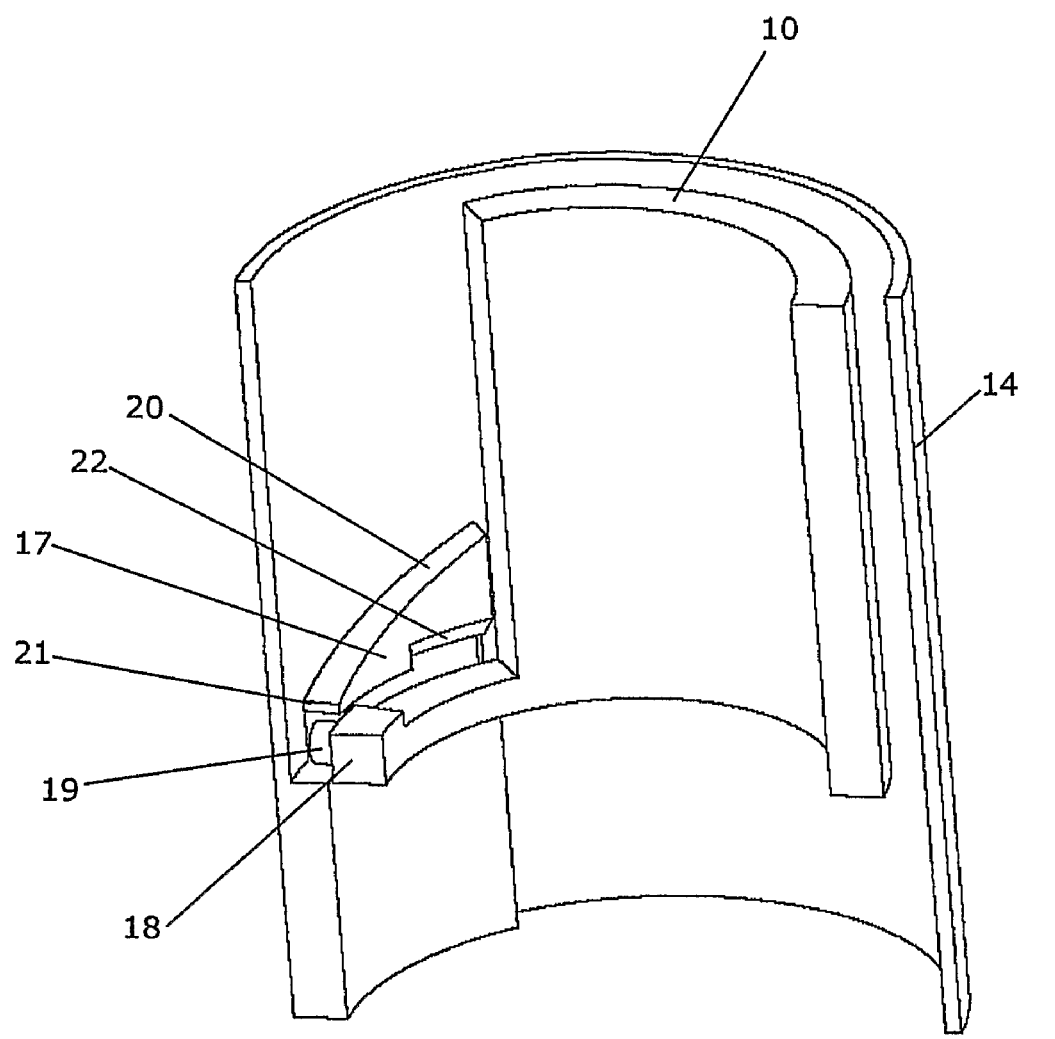

FIG. 7 shows part of an injection device according to a third embodiment of the invention. The Figure shows an inner part 10 and an outer part 14. The inner part 10 and the outer part 14 are adapted to be rotated relatively to each other during injection. The outer part 14 is provided with a wedge structure 17 and the inner part 10 is provided with a spring arm 18. During injection, in addition to the mutual rotation, the inner part 10 is moved in an axial direction indicated by the arrow. When the spring arm 18 reaches the wedge structure 17 a protruding part 19 of the spring arm 18 will engage an upper part 20 of the wedge structure 17. This will cause the spring arm 18 to be pressed in a direction opposite to the one indicated by the arrow, thereby introducing a tension in the spring arm 18. The tension is, thus, built up during injection. The protruding part 19 will subsequently be moved along the upper part 20 of the wedge structure 17 until it reaches the end 21 of the wedge structure 17. The protruding part 19 will then 'fall over the edge' to the position shown in FIG. 7, thereby releasing the tension which was previously built up in the spring arm 18. This sudden release of the tension produces a sound due to air being moved by the spring arm 18 and/or due to the protruding part 19 hitting a stationary part of the outer part 14. Thereby an audible feedback signal has been produced, and by positioning the wedge structure 17 in an appropriate manner, the feedback signal will indicate to the user that the set dose has been injected.

When a new dose is to be set, the protruding part 19 will pass the wedge structure 17 via a tapered part 22 on the wedge structure 17.

Figure 8:
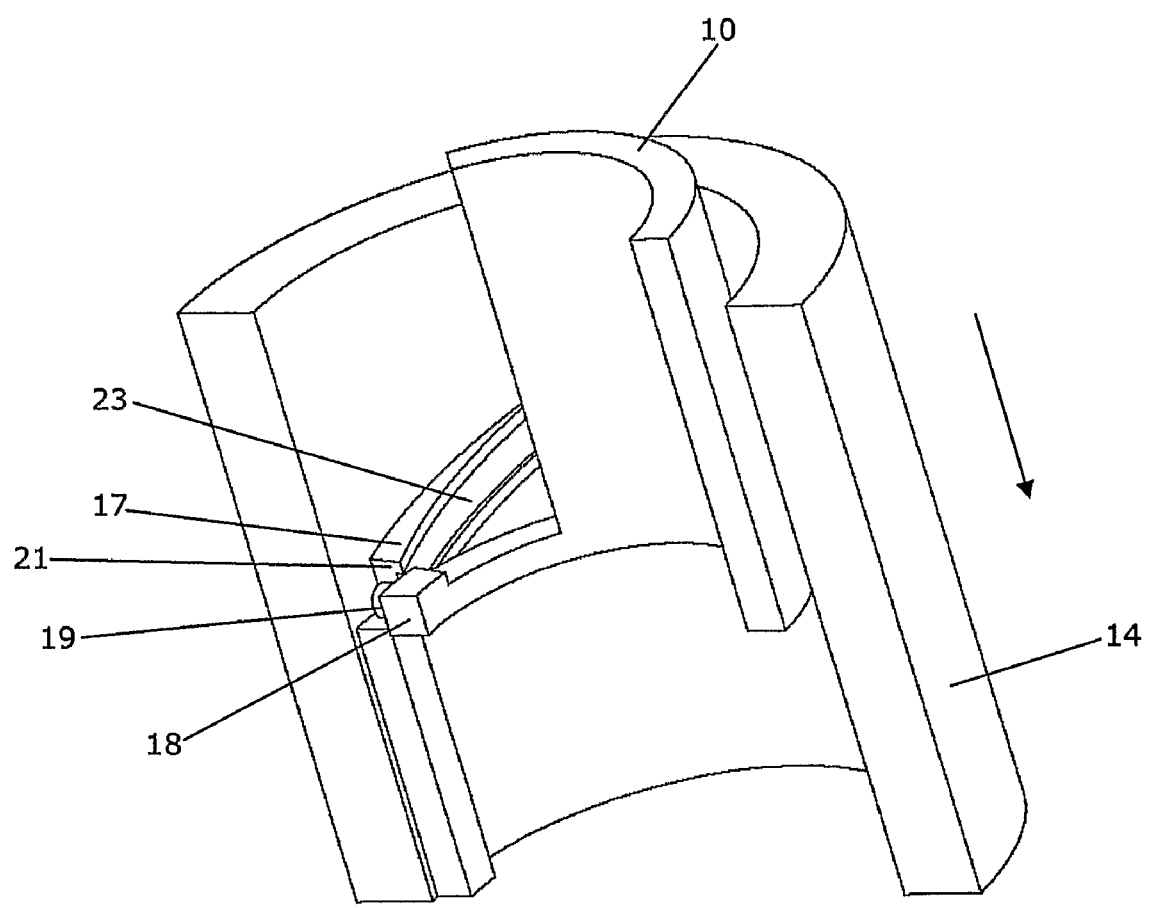

FIG. 8 shows part of an injection device according to a fourth embodiment of the invention. The fourth embodiment is very similar to the third embodiment shown in FIG. 7. FIG. 8 also shows an inner part 10 having a spring arm 18 and an outer part 14 having a wedge structure 17, the inner part 10 and the outer part 14 being adapted to rotate in relation to each other during injection. The spring arm is provided with a protruding part 19. During injection the inner part 10 moves relatively to the outer part 14 in a direction indicated by the arrow. When the spring arm reaches the wedge structure 17 the protruding part 19 will be caught in a track 23 and moved along this track 23. Due to the geometry of the wedge structure 17 this movement will result in the spring arm 18 being pressed in a direction away from the outer part 14, thereby introducing a tension in the spring arm 18. Thus, the tension is built up during the injection. When the protruding part 19 reaches the end 21 of the wedge structure 17 it will 'fall over the edge', thereby releasing the tension which was previously built up in the spring arm 18. This will result in an audible feedback signal being generated as described above.

When a new dose is to be set, the protruding part 19 will pass the wedge structure 17 by being lifted in an axial direction along the end 21 of the wedge structure 17.

Figure 9:
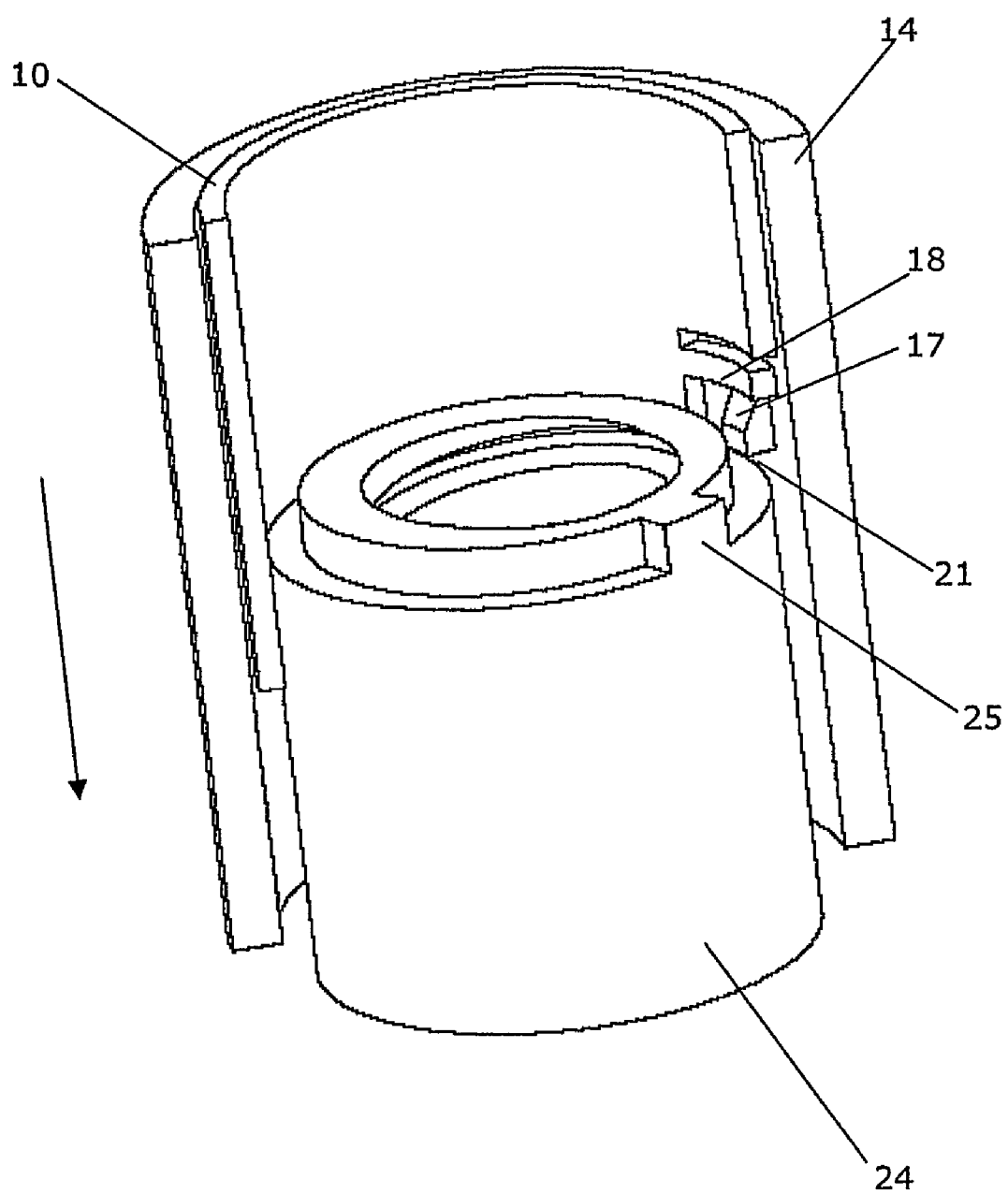

FIG. 9 shows part of an injection device according to a fifth embodiment of the invention. FIG. 9 shows an inner part 10 having a spring arm 18 and an outer part 14 having a wedge structure 17. During injection the inner part 10 will move relatively to the outer part 14 in a direction indicated by the arrow. However, in this embodiment the inner part 10 and the outer part 14 do not rotate relatively to each other. Instead the injection device comprises a rotational part 24 which rotates during injection relatively to the inner part 10 and the outer part 14. When the spring arm 18 reaches the wedge structure 17 it will be pushed in a direction away from the outer part 14 and towards the rotational part 24. Thereby it is moved into a path of a protruding part 25 on the rotating part 24. When the protruding part 25 is rotated to the position of the spring arm 18, it will therefore push the spring arm 18 out of its path again, thereby introducing a tension in the spring arm 18. When the protruding part 25 has passed the position of the spring arm 18, the spring arm 18 will again be free to move into the path of the protruding part 25, thereby releasing the tension which was previously built up in the spring arm 18. Thereby an audible feedback signal is generated due to air being moved be the spring arm 18 and/or due to the spring arm 18 hitting a wall of the rotational part 24, as described above.

Figure 10:
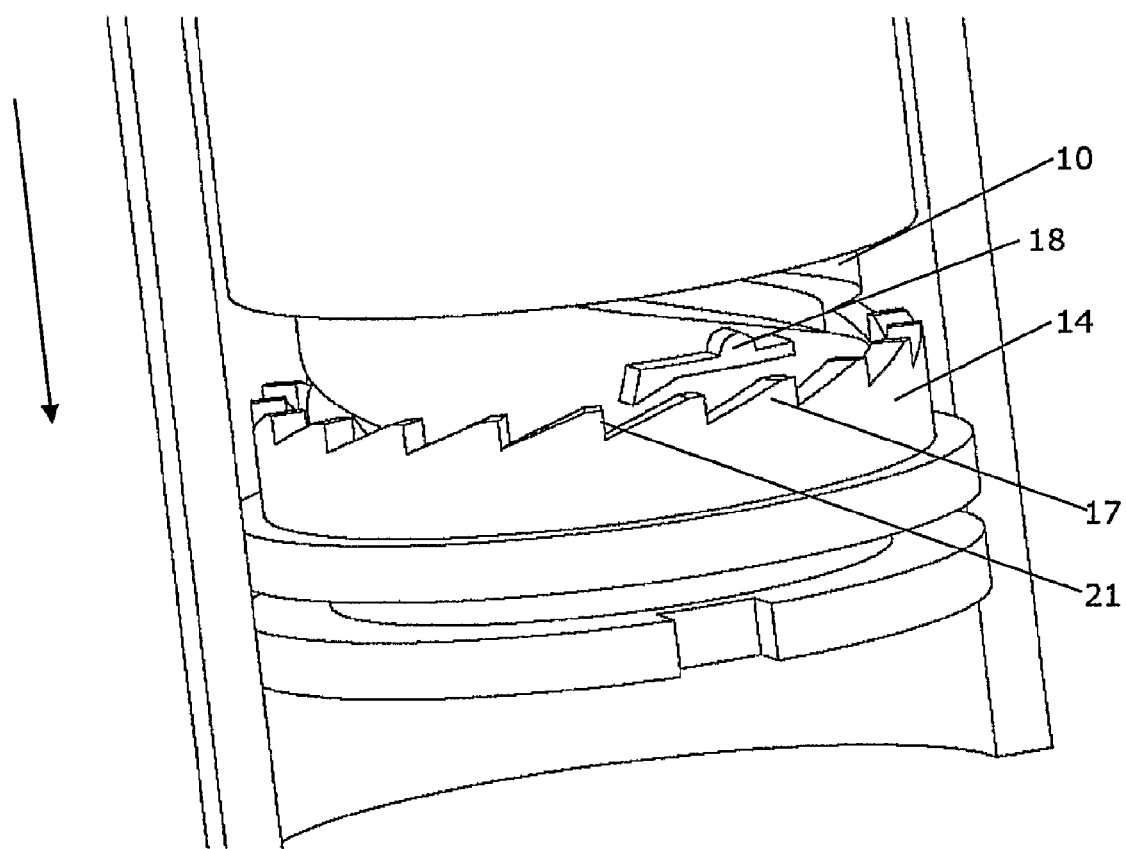

FIG. 10 shows part of an injection device according to a sixth embodiment of the invention. The Figure shows an inner part 10 having a spring arm 18 and an outer part 14 having a wedge structure 17. The inner part 10 and the outer part 14 are adapted to rotate relatively to each other during injection. Furthermore, the inner part 10 moves relatively to the outer part 14 in the direction indicated by the arrow during injection. When the spring arm 18 reaches the wedge structure 17 it will be caught by one of the wedges. Due to the geometry of the wedge structure 17 and to the continued rotational and axial movement (in the direction of the arrow) of the inner part 10, the spring arm 18 will be pressed in a direction opposite the direction indicated by the arrow, thereby introducing a tension in the spring arm 18. Subsequently when the spring arm 18 reaches the end 21 of the wedge it will 'fall over the edge', thereby releasing the previously built up tension. This will cause an audible feedback signal to be generated as described above.

Figure 11:
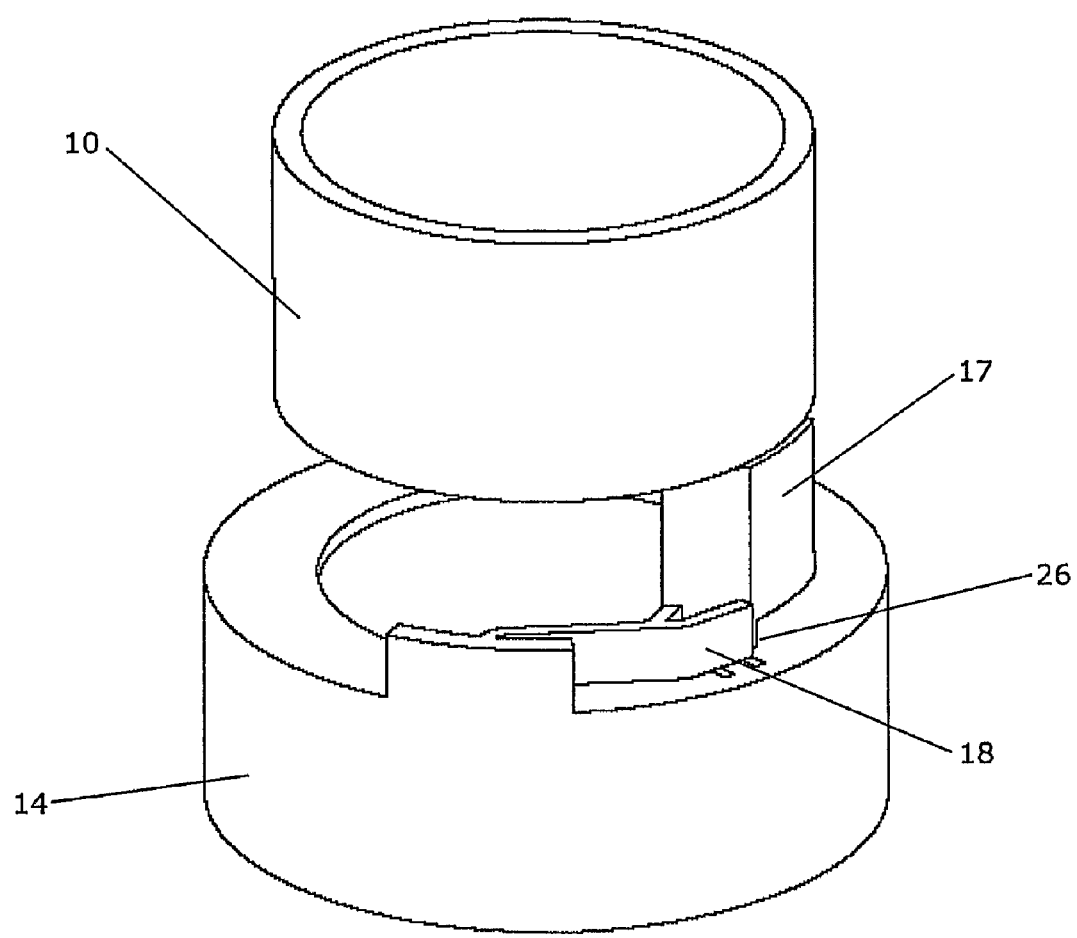
FIG. 11 shows part of an injection device according to a seventh embodiment of the invention having a spring arm and a release mechanism.

FIG. 11 shows part of an injection device according to a seventh embodiment of the invention. The Figure shows an inner part 10 having a wedge structure 17 and an outer part 14 having a spring arm 18 and a locking mechanism (not shown in FIG. 11). The inner part 10 and the outer part 14 are adapted to rotate in relation to each other during setting of a dose and during injection. The inner part 10 is typically a scale drum or is adapted to rotate along with a scale drum during setting of a dose and during injection. Thus, when a dose is set the inner part 10 is rotated in such a way that the wedge structure 17 presses the spring arm 18 outwards and into engagement with the locking mechanism, thereby introducing a tension in the spring arm 18. Thus, in this embodiment the tension is introduced during setting of the dose. The locking mechanism will maintain the spring arm 18 in the tensed position during the remaining setting of the dose and during the main part of the injection.

However, when the inner part 10 is returning to the initial position a release mechanism 26 on the wedge structure 17 releases the locking mechanism, thereby releasing the tension which was previously built up in the spring arm 18. Thereby an audible signal is generated as described above, and because the locking mechanism is released when the inner part 10 is returning to the initial position, this audible signal indicates that the set dose has been injected.

Figure 12:
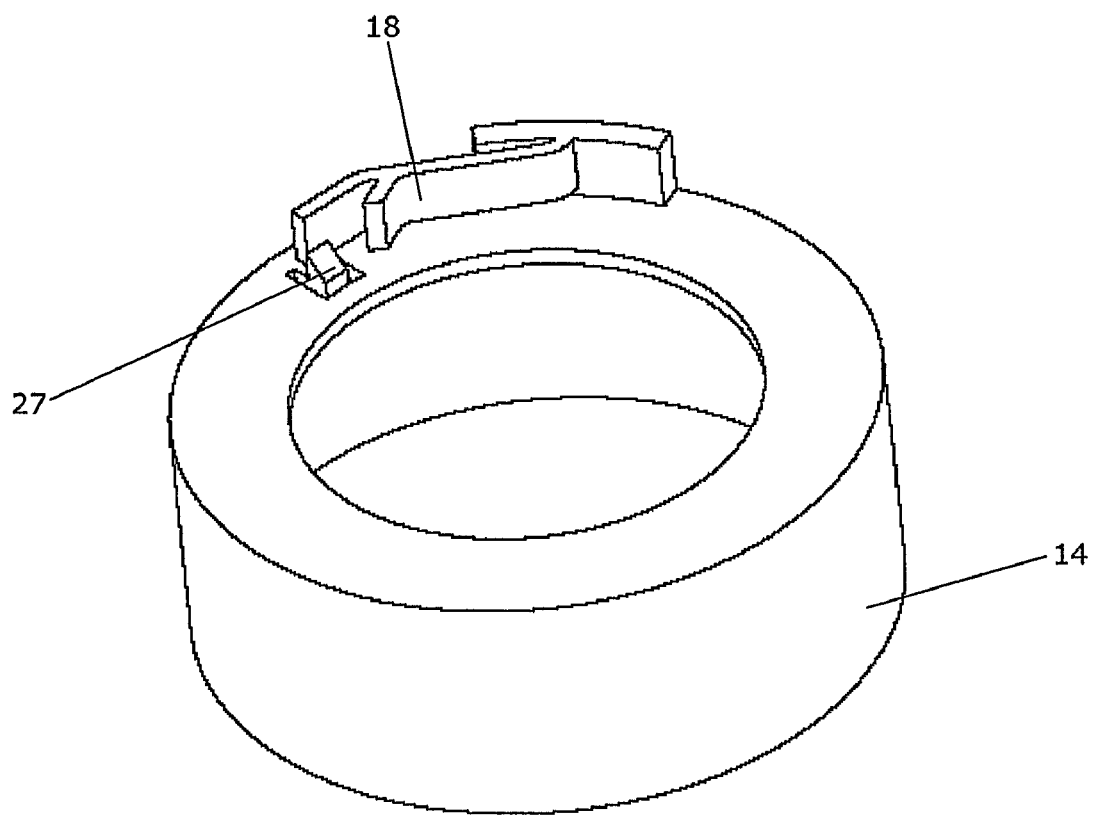
FIG. 12 shows an outer part of the injection device of FIG. 11 from a different angle.

FIG. 12 shows the outer part 14 of the injection device of FIG. 11. The outer part 14 has a locking mechanism 27 which is in a locking position, i.e. it engages the spring arm 18. Thus, in FIG. 12 the spring arm 18 is tensed. When the inner part (not shown) approaches the outer part 14 as described above, the release mechanism (not shown) will push the locking mechanism 27 downwards, and the tensed spring arm 18 will then restore its relaxed position, i.e. it will move towards the centre of the outer part 14. Thereby the tension built up in the spring arm 18 is suddenly released.

Figure 13:
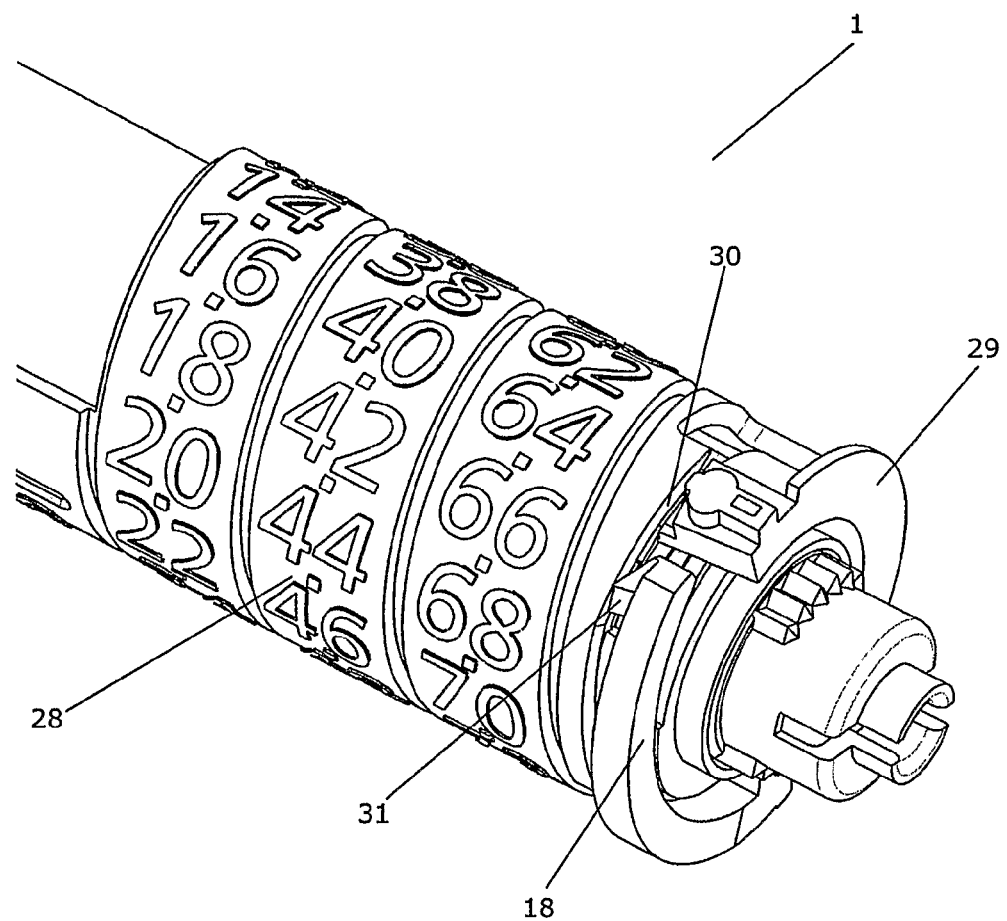
FIGS. 13-15 show part of an injection device according to an eighth embodiment of the invention having a spring arm, at various points in time.

FIG. 13 shows part of an injection device 1 comprising a scale drum 28 and a spring arm member 29 positioned at the proximal end of the injection device 1. The spring arm member 29 is provided with a spring arm 18 which may be deflected in a proximal direction, i.e. away from the scale drum 28.

During injection of a set dose, the scale drum 28 performs a rotational movement as well as an axial movement towards the spring arm member 29. This movement will eventually cause an upper portion 30 of the scale drum to abut a protrusion 31 of the spring arm 18. As the scale drum 28 continues the rotational and axial movement, the spring arm 18 is deflected in a proximal direction, thereby causing a tension to be built up in the spring arm 18.

FIG. 13 shows a situation where the upper portion 30 of the scale drum 29 and the protrusion 31 of the spring arm 18 abut, and a tension has started to build up in the spring arm 18.

Figure 14:
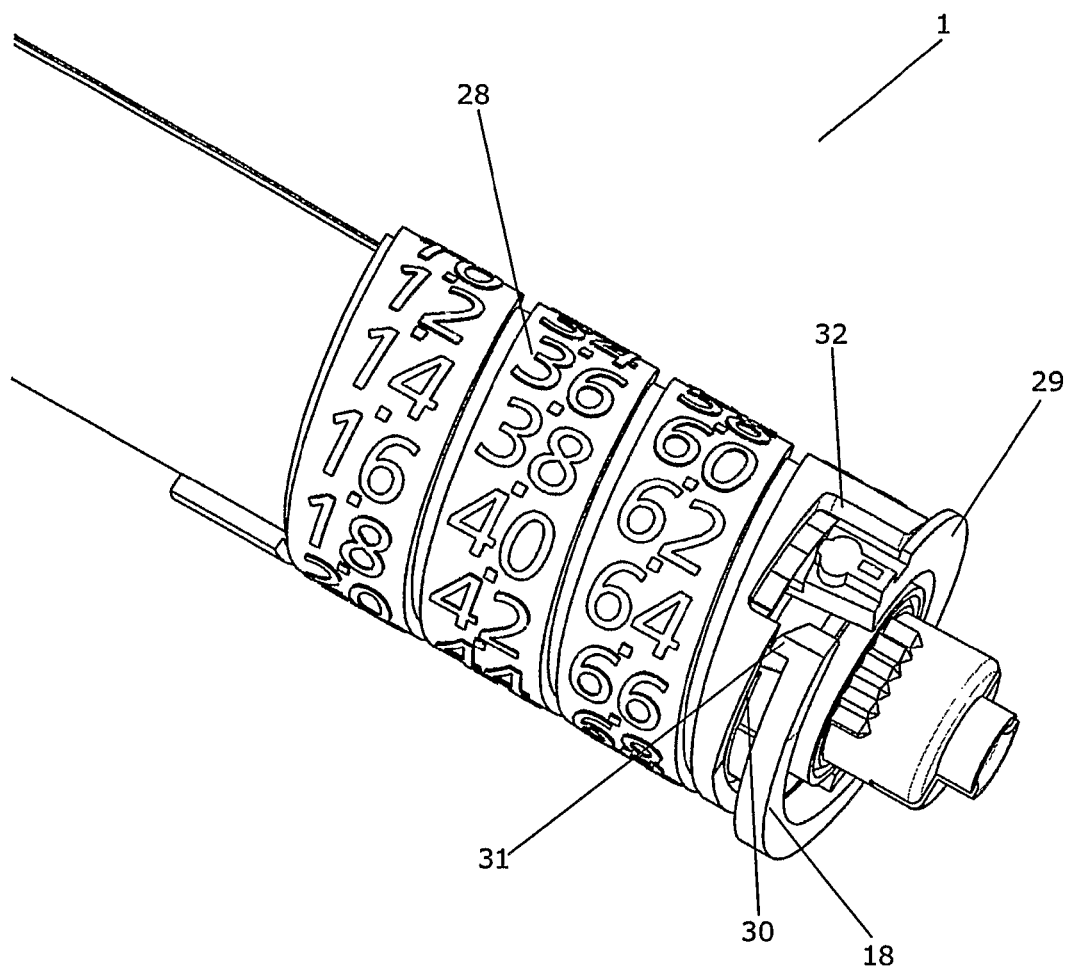

FIG. 14 shows the injection device of FIG. 13. In FIG. 14 a tension has been built up in the spring arm 18 as described above. The protrusion 31 of the spring arm 18 is positioned very near a recess 32 formed in the scale drum 28. Thus, further rotation of the scale drum 28 will cause the protrusion 31 to 'fall over the edge' into the recess 32. Thereby the tension which has previously been built up in the spring arm 18 is released, and an audible feedback signal is generated by vibrating air and/or by the protrusion 31 hitting a lower edge of the recess 32.

Figure 15:
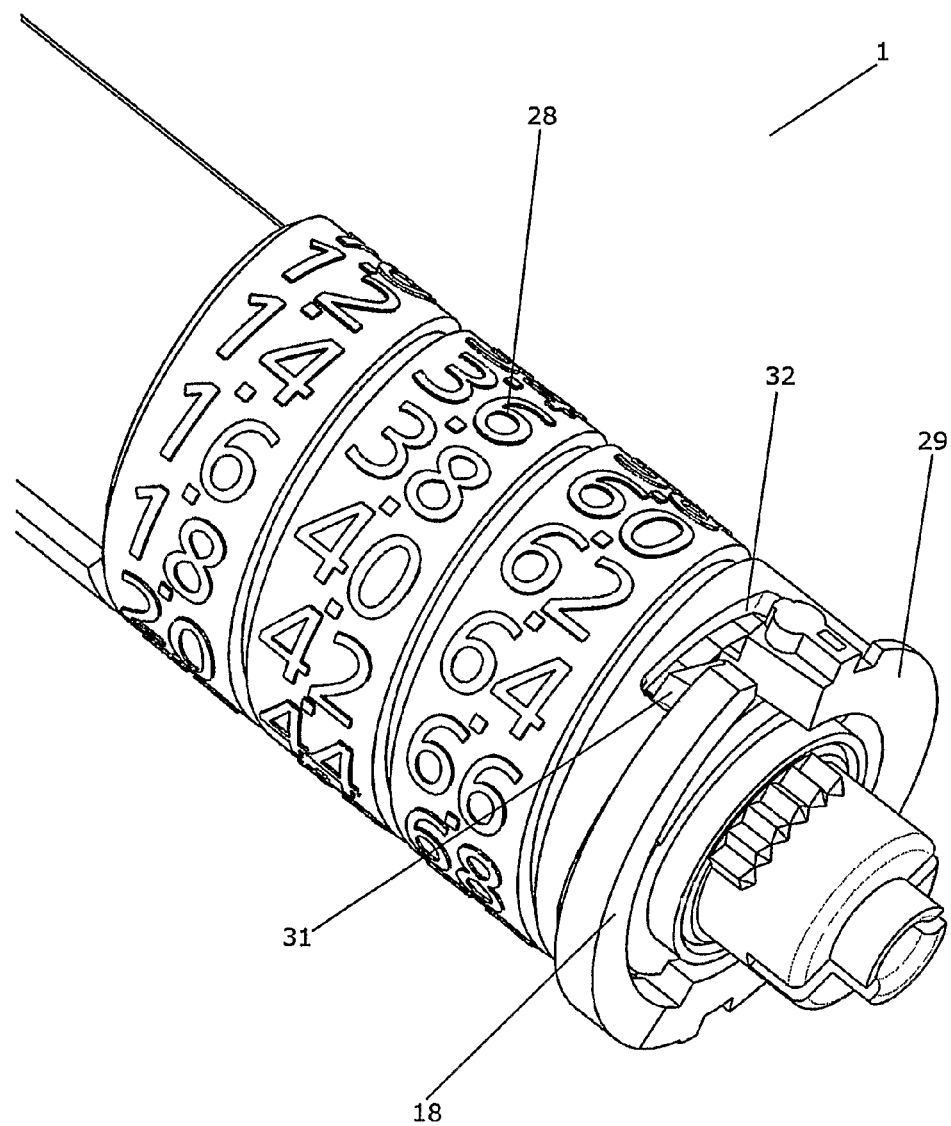

This situation is illustrated in FIG. 15, showing the injection device 1 of FIGS. 13 and 14 in a situation where the tension previously built up in the spring arm 18 has been released as described above.

When a new dose is to be set, the feedback mechanism needs to be reset in order to be able to provide an audible feedback signal when the subsequent dose has been injected. This is done by leading the protrusion 31 of the spring arm 18 via a path or track (not visible in FIGS. 13-15) positioned behind the upper portion 30 of the scale drum 28 during the next dose setting. When the set dose is sufficiently large, the scale drum 28 and the spring arm member 29 will be sufficiently spaced apart to allow the protrusion 31 to be positioned above the upper part 30 of the scale drum 28. Thereby the feedback mechanism has been reset, i.e. the spring arm 18 is once again ready for being deflected in a proximal direction as described above.

The injection device shown in FIGS. 13-15 is particularly suitable for having a dose delivering mechanism which is adapted to be operated by means of a mechanically biased mechanism, such as a spring.

Some preferred embodiments have been shown in the foregoing, but it should be stressed that the invention is not limited to these, but may be embodied in other ways within the subject matter defined in the following claims.

The invention claimed is:

1. An injection device comprising:
a housing having a longitudinal axis,
a dose setting member being operable to set a desired dose to be injected,
a piston rod being adapted to cooperate with a piston so as to cause a set dose to be injected from an ampoule, and
a dose delivering mechanism being adapted to operate the piston rod in such a way that a set dose is injected by a mechanically biased mechanism comprising at least one spring, the dose delivering mechanism further being adapted to provide a tactile feedback signal to a user only at the end of injection of a set dose,
wherein first and second parts of the injection device are adapted to perform a relative rotational movement around a longitudinal axis with respect to each other during injection of a dose, and wherein said relative rotational movement causes at least two parts of the injection device to abut or engage, said abutment or engagement causing the tactile feedback signal to be generated.

2. An injection device according to claim 1, wherein the tactile feedback signal comprises an audible signal.

3. An injection device according to claim 1, wherein the tactile feedback signal comprises a tactile signal.

4. An injection device according to claim 1, wherein the abutment or engagement is caused by a change in a rotational velocity of at least one part of the dose delivering mechanism.

5. An injection device according to claim 4, further comprising a ratchet operating the piston rod and having a threaded portion being adapted to engage with a part of the dose delivering mechanism, and wherein the change in a rotational velocity is generated by a change in the pitch of the threaded portion of the ratchet, said change in the pitch in return causing a change in a translational velocity of said part of the dose delivering mechanism, said change in translational velocity causing at least two parts of the injection device to abut, thereby causing the tactile feedback signal to be generated.

6. An injection device according to claim 4, wherein the dose delivering mechanism comprises a first dose part and a second dose part, the first dose part being adapted to rotate relatively to the housing during injection of a dose and the first dose part comprising structure for engaging the second dose part at the end of injection of a set dose, thereby causing the second dose part to rotate along with the first dose part, and wherein the tactile feedback signal is generated by the resulting rotational movement of the second dose part.

7. An injection device according to claim 6, wherein the second dose part is positioned between the first dose part and the housing.

8. An injection device according to claim 1, wherein the tactile feedback signal is generated as a result of an abutment between two parts of the dose delivering mechanism performing a relative rotational movement.

9. An injection device according to claim 8, wherein the tactile feedback signal is generated by a tensed part whereby the tactile feedback signal is provided by releasing a tension which has previously been introduced in a part of the injection device, the release of the tension being caused by the abutment between the two parts.

10. An injection device according to claim 9, wherein the tensed part comprises a spring structure.

11. An injection device according to claim 9, wherein the tension is introduced during dose setting.

12. An injection device according to claim 9, wherein the tension is introduced during injection of a dose.

* * * * *